United States Patent [19]
Dilenge et al.

[11] Patent Number: 5,665,234
[45] Date of Patent: Sep. 9, 1997

[54] MICRO-FILTER DISC AND A METHOD FOR ITS PRODUCTION

[75] Inventors: Angelo Dilenge, Siershan, Germany; Peter Grüter, Regensdorf, Switzerland

[73] Assignee: Lukopat AG, Glarus, Switzerland

[21] Appl. No.: 530,095

[22] PCT Filed: Mar. 24, 1994

[86] PCT No.: PCT/EP94/00947
§ 371 Date: Nov. 15, 1995
§ 102(e) Date: Nov. 15, 1995

[87] PCT Pub. No.: WO94/22555
PCT Pub. Date: Oct. 13, 1994

[30] Foreign Application Priority Data

Mar. 29, 1993 [DE] Germany ............... 93 105 152.8

[51] Int. Cl.$^6$ .................................. B01D 27/08
[52] U.S. Cl. ............ 210/496; 210/500.25; 210/500.26; 210/501; 210/503; 210/510.1
[58] Field of Search .................... 210/503, 496, 210/510.1, 500.25, 500.26, 501

[56] References Cited

U.S. PATENT DOCUMENTS 583,698  6/1897  Bennett ........................... 210/496
4,968,487 11/1990 Yamamoto et al. .......... 210/504 X
4,980,334 12/1990 Brennan ......................... 502/263

*Primary Examiner*—W. L. Walker
*Attorney, Agent, or Firm*—Bardehle, Pagenberg, Dost, Altenburg, Frohwitter, Geissler & Partners

[57] ABSTRACT

The invention at hand relates to a micro-filter disc based on kieselguhr, also known as diatomaceous earth, particularly for a complete sterilization of water. The micro-filter disc contains at least two kinds of silicately bonded kieselguhr at least one of which is pre-calcined and later burnt or sintered. The micro-filter disc has pore sizes in preferred magnitudes of 0.1 to 0.3µ whereby bacteria are mechanically and safely retained. A method is disclosed making possible the use of three kinds of kieselguhr and kaolin in connection with a careful drying and sintering thereafter. Thereby, it is possible to produce discs having diameters larger than 35 cm and a thickness of 1 to 1.5 cm. Such discs can be cleaned by way of rotating brushes slightly scraping off the discs. This enhances a simple construction of self-cleaning filter installations. The thus constructed filter installations require very little service and can be serviced by inexperienced operators.

38 Claims, 2 Drawing Sheets

MICRO-FILTER DISC AND A METHOD FOR ITS PRODUCTION

BACKGROUND OF THE INVENTION

The invention at hand relates to a micro-filter disc, particularly for the sterilization of water, and a method for its production.

During the mechanical sterilization of water by means of a microfilter, it is essential that the pore size of the filter device be small enough and be of a typical size of 0.4 to 0.5µ so that bacteria are safely re-trained. Ceramics or other materials having suitable pore sizes, up to now, could not be produced in just any desirable form so that filters with large surfaces and having good filtering effectiveness could only be produced under large expenditures and poor serviceability. The until now used large surface area filter columns and having been made of ceramics are difficult to clean, whereby known filter installations, commonly, have to be opened frequently and have to be cleaned by hand.

Reference is particularly made to the European patent application 92 810 843, wherein a self-cleaning filter installation is being described having been provided with a cleaning unit being moveable relative to the filter surfaces and being movable thereagainst for the scraping off of filter material. Such filters can be regularly cleaned in an assembled state by cleaning brushes being driven from the outside to thereby substantially simplify the maintenance.

An object of the invention at hand is the provision of a flat micro-filter disc having a large surface area which, for example, can be installed in a self-cleaning filtering installation. Furthermore, a suitable method for the production of such a micro-filter disc is indicated.

To attain this object, a micro-filter disc is provided which is produced on a kieselguhr (diatomaceous earth) basis and contains at least two silicately bonded kinds of kieselguhr of which at least one is pre-calcined and later being sintered, and whereby the micro-filter disc exhibits of pore size in the magnitude of 0.05 to 0.5µ, preferably 0.1 to 0.3µ. It has been discovered that the presence of a kind of a pre-calcined kieselguhr assures the stability of the micro-filter disc during its production and forms a framework for the provision of at least a further kind of kieselguhr of a different kind, whereby a stable form is obtained having the desired pore sizes. Particularly, a monolithical round microfilter disc can be produced having a diameter of at least 25 cm, preferably at least 35 cm. Such a disc can have a thickness of 0.5 to 2 cm, preferably about 1 to 1.5 cm. A good filtering effect is obtained with a simultaneous good breaking strength of the disc having a thickness of about 0.5 cm. A typical permeability of the disc, according to the invention, stands at 0.5 to 0.7 liter (midm$^2$), preferably at 0.6.

It is preferred that the micro-filter disc has a central round opening having a diameter of 3 to 15 cm, preferably 6 to 10 cm. Because of the presence of this opening, several micro-filter discs can be superimposed upon each other on a central column, wherein the column can rotate or have a rotatable shaft to facilitate a relative movement between the micro-filter discs.

In order to be able to tightly install such micro-filter discs in a filtering installation, the outer and inner margins of the micro-filter disc have to be cut to exact tolerances which can be obtained by high pressure water-jet cutters. The margins are preferably provided with a sealing layer which also overlaps around the disc on at least one side by about 1 to 8 mm, preferably by 3 to 5 mm. In this manner, the disc can be mounted sealingly with its margins as well as with an underlayer. The seals should have a thickness of 1 to 3 mm in order to accommodate any size changes of the disc.

It is preferred that the filter disc exhibit open pores on its upper surface to enhance an automatic cleaning of the upper surface from time to time, which surface should be soft enough to obtain an abrading by means of a cleaning brush. Such cleaning brush can have man-made bristles, for example, particularly nylon or precious metal bristles, whereby the aim is to obtain an upper surface cleaning by abrading a layer having a thickness of about 0.1 to 5µ with just a few working strokes. This abrading should be obtained after about one to twenty relative movements between the upper surface and the cleaning brush. The abraded substance can thereafter be rinsed away during a rinsing cycle and will not permeate through the filter disc.

In order to kill invading bacteria and in order to avoid the growth of bacteria retained on the upper surface through the micro-filter disc, the disc preferably contains parts of a non-washable silver oxide. A disc having especially great stability and good filtering effectiveness can be obtained through the use of least three different kinds of kieselguhr and a portion of kaolin. One kind of the kieselguhr is pre-calcined and at least one other kind contains particularly many small particles, about 15% of the particles having a size below 2µ.

In a preferred embodiment, the micro-filter disc contains 6 to 12 percent by weight, preferably 9 percent by weight of a pre-calcined and commonly with the other components again sintered kieselguhr, 25 to 30 percent kaolin, and the remainder being a further kinds of kieselguhr as well as possibly silver oxide and other smaller amounts of production mandated components. The percent by weight indicator relates to the weight of the finished sintered and dried disc.

The production of such a micro-filter disc is undertaken by way of a method involving the following steps:

a. The following is being mixed: At least 6 to 12 parts by weights, preferably 9 parts by weight, of an already calcined kind of kieselguhr, 25 to 35 parts by weight, preferably 30 parts by weight of kaolin and 53 to 69 parts by weight, preferably 61 parts by weight, of a further non- or at least very little calcined kind of kieselguhr;

b. The mixture is stirred-up with 200 to 250 parts by weight, preferably 225 parts by weight of water to which is added 0.2 to 0.35 parts by weight, preferably 0.27, a liquefying agent to decrease the surface tension and an organic binding agent at 0.4 to 0.8 parts by weight, preferably 0.5 to 0.7 parts by weight;

c. The mixture is being stirred until a definite change in viscosity occurs, preferably in 12 to 15 hours;

d. The stirred and finished mixture is poured into a mold having been made of a moisture absorbing material such as plaster of paris;

e. The mixture is slowly being dried, preferably over a period fo time of 8 to 25 days, particularly 10 to 20 days;

f. The dried mixture is now being sintered by being burnt at a temperature of 1000° to 1050° C., particularly at 1035° C.

By way of examples and as will be explained later on, the liquefying agent in combination with the prolonged stirring results in a very even distribution of the fine particles of the differing kinds of kieselguhr and the kaolin throughout the mixture. The organic binding agent aids in the coherence of the unsintered form while drying inside or outside the mold, while the already calcined portion of the kieselguhr forms a stable framework and thereby assures a form stability (green strength) of the still unsintered disc. Stabilized by the portion of the calcined kieselguhr, and held together by the organic binding agent, the remaining components fall in line in a very homogenous order, whereby the desired porosity is obtained. In this manner, it is possible to produce monolithic discs having the desired porosity and diameters not achievable until now and free of cracks.

In a preferred example, the following components are being used expressed in parts by weight:

About 40.72 of a first kind of non-calcined or at least very little calcined kieselguhr, about 9.05 of a second kind of calcined kieselguhr, about 20.82 of a third kind of a non-calcined or at least very title calcined kieselguhr, and about 29.41 of kaoline.

Herein, kinds of kieselguhr are employed having differing distributions of particle sizes, so that as a whole, a desired porosity in the disc in the magnitude of $0.05\mu$ to $0.5\mu$, preferably $0.1$ to $0.3\mu$, is obtained.

In order to avoid any bacteria being retained on the upper surface and later on being able to grow through the ceramic structure, silver oxide is added to the mixture at 0.2 to 0.5 parts per weight, preferably at about 0.36.

In order to avoid any cracking of the micro-filter disc during its production, the choice of the mold is very important. It is preferred that the material for the mold should be minimally moist plaster of paris into which mold the finished mixture is being poured. Plaster of paris is a material being water absorbable. When a completely dry plaster of paris mold is used, it absorbs water rather quickly from the mixture and can result in a possible development of cracks. Therefore, a minimally moist plaster of paris is preferred.

In order to produce discs having openings through the center, the form must be provided with a control core which is instrumental in forming the opening. Also, in this area, formation of cracks can easily occur. Therefore, the core should consist of a yieldable and absorbent material which yields to any deforming of the disc while it is drying. A hollow cylinder made of paper or card board is particularly useful because it initially absorbs moisture but during drying of the mixture later on can undergo a minimal deforming and, finally, is easily separable from the disc.

During the process of sintering the thus pre-manufactured and pre-dried disc, there is commonly an increase in the density of the upper surface which for the intended purpose, namely, the filtering of fluids, is not permeable enough and, therefore, unsuitable. Therefore, after sintering, the denser upper layer is being removed by a scraping tool, which layer commonly has a thickness of about $5\mu$.

Finally, the disc may be cut to an exact measure. This can be done by the use of a high pressure water-jet cutters. In order to be able to install the discs in a sealing manner in a filter installation, the outer and inner margins of each disc are provided with sealing layers which overlap onto at least one side of the disc. The sealing layer material is preferably based on silicone which can be glued to the disc.

Following is a detailed description of the invention with reference being made to the drawings and to particular examples with the attendant advantages and modifications.

Figure 1:
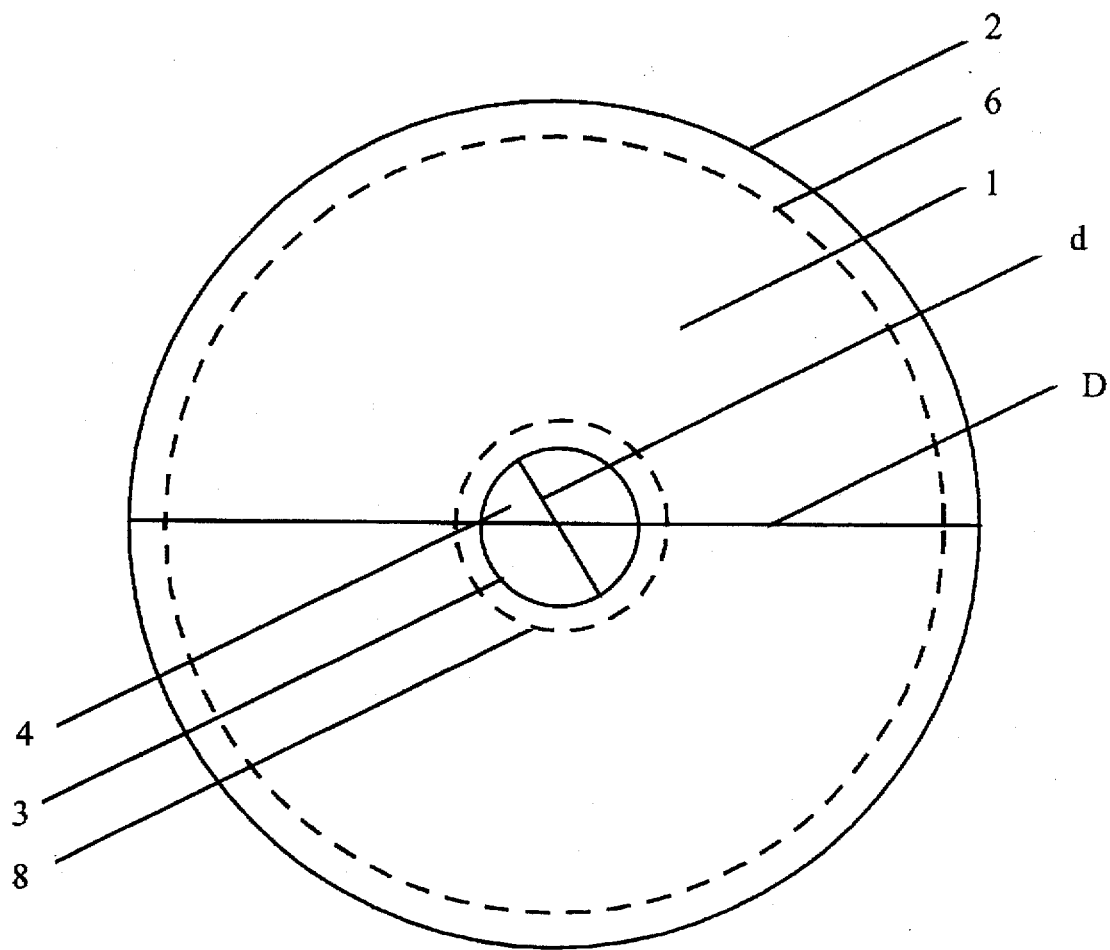
FIG. 1 shows a top view of the inventive disc.
Figure 2:
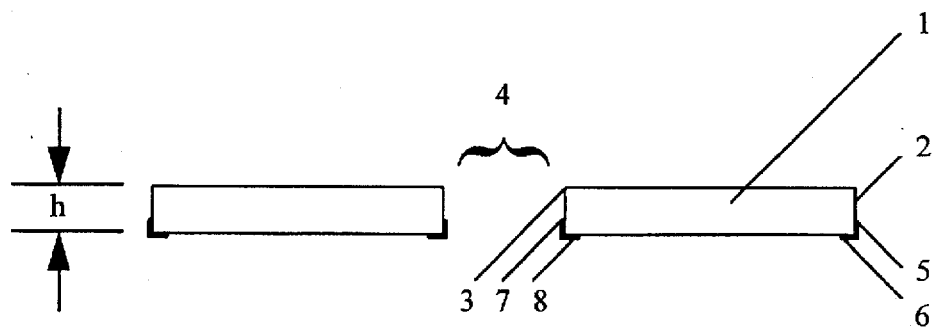
FIG. 2 is a cross-section through such a disc.

An embodiment of disc 1 is illustrated in FIGS. 1 and 2 and has an outer diameter D of about 40 cm and an inner diameter of the central opening 14 of about 6.5 cm. As can be seen from FIG. 2, the outer margin 2 of disc 1 is provided with a seal 5, which with a section 6 also overlaps onto the underside of disc 1. Also, the inner margin 3 of disc 1 is provided with a seal 7, which, with a section 8 also overlaps onto the underside of disc 1. Both seal section 6,8 on the underside of disc 1 enhance a sealing of the disc 1 when deposited on a structure supporting the same, while the seals 5,6, provided on the inner margin 3 and the outer margin 2, are in a sealing engagement with a not shown container wall and a not shown inner cylindrical column. The seals also serve for the absorption of temperature induced minimal expansions of the disc. The seals 5,7 on the outer and the inner margins, respectively, can also be applied separately from the seals 6,8 located on the underside of the disc, preferably, by gluing.

Figure 3:
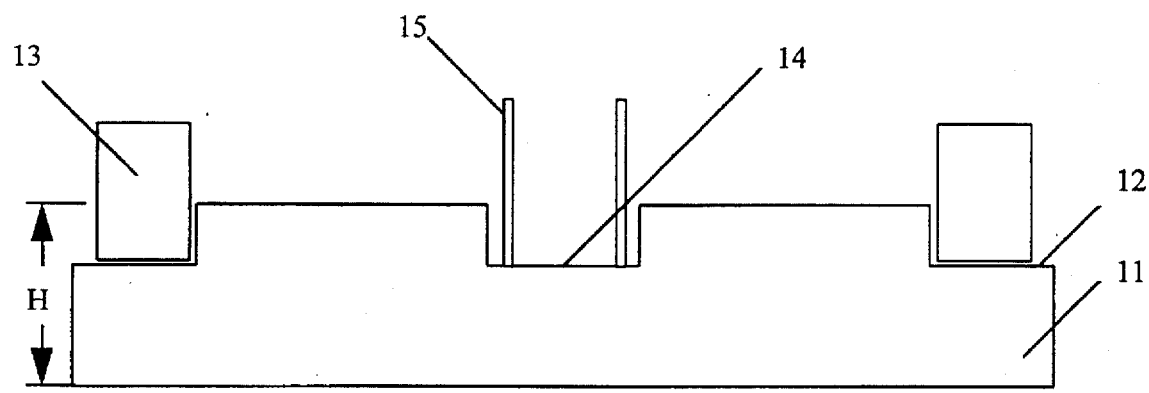
FIG. 3 shows a suitable mold for the production of the inventive disc.

The mold illustrated in FIG. 3 aids in the production of the inventive disc 1. The base plate 11 has a height of about 50 to 70 mm and is provided with an outer ring-depression 12 into which a ring-like mold part 13 can be inserted. The base plate should have a height H of $\frac{1}{16}$ to $\frac{1}{10}$, preferably $\frac{1}{8}$ of the diameter D of disc 1. Base plate 11 and ring-like mold part 13 consist of plaster of paris material which, when filling the mold, should not be completely dry. The base plate 11 also has a circular or ring-like depression 14 in the center into which a hollow cylindrical core 15 can be inserted. The core 15 is preferably made of paper or card board.

The mold, having been assembled from base plate 11, ring-like mold part 13 and cylinder form insert 15, is now ready for the production of disc 1 by pouring the requisite amount of ceramic mass into the mold. The mold absorbs a portion of the fluid of the poured mass and thereby supports a slow drying process. In order to avoid a sticking of the poured mass to the plaster of paris mold, a sliding medium, particularly talcum powder, should be applied to the mold. After about two to five hours, the thus formed discs can be removed from the mold and should be placed on a flat and absorbent support layer, preferably again made of plaster of paris, for further drying. In order to avoid any cracks from developing, the drying should be undertaken with temperatures between 30° and 50° C., preferably between 35° to 40° C., so that the drying process can stretch to about two to three weeks.

After drying, the disc is being sintered during an overall burn period of 10 to 15 hours while holding maximum temperature peaks of about 1035° C. for about 20 minutes.

Following again are described the ingredients for the ceramic mass and a method of mixing the same by way of an example which is considered to be very favorable.

Starting with 4.4 liters of water, a liquefying agent is being added under constant stirring, which will lower the surface tension, and 12 g of an organic binding agent are being added. Thereafter, 900 g of first kind of kieselguhr, 200 g of a second pre-calcined kind of kielguhr, 460 g of a third kind of kieselguhr, and 650 g of kaolin are all added. After intensive stirring, also 8 g of silver oxide is being added. In order to achieve a thorough homogenization of the whole mixture, the same is further stirred for about 15 to 18 hours until the mixture becomes pourable when the viscosity all of a sudden drops by about 10 to 20%, that is, the mixture becomes thinner. When pouring the liquid mixture, the PH value should be about 9.

The individual components, particularly by the liquefying agent and the organic binding agent can themselves be added already dissolved in water, whereby, the overall amount of water in the mixture should be about 5 liters.

The following table contains indications of the differing kinds of kieselguhr being used with regard to their compositions and particle size. Kieselguhr, also known as diatomaceous earth, is a naturally occurring material which, by way of geological processes, evolved from Kieselalgae. Such Kieselguhr are obtainable under the Trademark "CELITE" from the Manville International Corporation, Denver, USA which are offered in corresponding compositions and in fine granular selections.

| PROPERTY | Kieselguhr 1 | Kieselguhr 2 | Kieselguhr 3 |
| --- | --- | --- | --- |
| Pre-Calcined | No | Yes | No |
| $SiO_2O_2$ | 85.8 | 85.8 | 89.3 |
| $Al_2O_3$ | 3.8 | 3.8 | 4.2 |
| $Fe_2O_3$ | 1.2 | 1.2 | 1.4 |
| $TiO_2$ | 0.2 | 0.2 | 0.2 |
| CaO | 0.5 | 0.5 | 0.6 |
| MgO | 0.6 | 0.5 | 0.6 |
| $Na_2O$ oder $K_2O$ | 1.1 | 1.1 | 3.5 |
| $P_2O$ | 0.2 | 0.2 | |

The discs according to the invention are especially suitable for self-cleaning filter installations because of their monolithic flat form as described in the European patent application 93 810 843.0, dated Mar. 11, 1992. Full reference is made to that application and its complete contents to avoid being repetitious. According to the therein described embodiment, two filter discs are supported in a support frame to thereby form a filter element which is being supplied with unclean water from the outside, is being cleaned inside, and clean water is discharged thereafter. Many such filter discs are superimposed on each other to form a large filter element having a large surface area and, therefore, has a large through-flow per time unit. The flat shape of the discs enhances the cleaning by rotating brushes having been fastened to a control shaft which has been projected through the central opening of each disc. Thin upper surface layers are scraped from the discs during each cleaning cycle to thereby restore the original characteristics of a fresh filter disc. By way of ultra-sound or other surveying techniques, it can be determined when the discs have been scraped off to a thickness of about 0.5 cm, for example. When this occurs and should the disc remain in further service, a danger of fracture is present and it should be replaced. Because of their monolithic structure, the discs are easy to exchange and do not require a complicated structure to be supported and sealed against each other. They are, therefore, especially suitable for an economical operation in filter installations for the sterilization of water. The particularly small pores enhance a safe mechanical retention of bacteria. To enhance the quality of taste, an activated charcoal filter could be placed in operation in series with the filter. Also, the usual disinfectant medium can be provided between the filter discs on their "clean" sides.

We claim:

1. A micro-filter disc including kieselguhr for the sterilization of water wherein:
   (a) said micro-filter disc comprises at least two types of silicately bonded kieselguhr, at least one of which is pre-calcined and burnt later; and
   (b) said micro-filter disc comprises pore sizes of a magnitude of 0.05 to 0.5µ.

2. A micro-filter disc according to claim 1, wherein said micro-filter disc is monolithical, round, and has a diameter of at least 25 cm.

3. A micro-filter disc according to claim 1 wherein said micro-filter disc further comprises a thickness of 0.5 to 2 cm.

4. A micro-filter disc according to claim 1 wherein said micro-filter disc has a central opening having a diameter of 3 to 15 cm.

5. A micro-filter disc according to claim 1, wherein an outer and an inner margin of said micro-filter disc have been cut to measure.

6. A micro-disc filter according to claim 1, wherein an outer and an inner margin of said micro-filter disc have been provided with seals which overlap said micro-filter disc to one side by 1 to 8 mm.

7. A micro-filter disc according to claim 1, wherein said micro-filter disc comprises an open pore upper surface which is soft to an extent that cleaning brushes having NYLON bristles or precious metal bristles can scrape off from 0.1 to 0.5µ in few working cycles.

8. A micro-filter disc according to claim 1, wherein said disc contains portions of non-washable silver salts.

9. A micro-filter disc according to claim 1, wherein said disc contains at least three portions of kieselguhr and a portion of kaolin.

10. A micro-filter disc according to claim 1, wherein said disc contains about:
   6 to 12 percent by weight kieselguhr, which is pre-calcined and after that burned again together with the remaining components;
   25 to 30 percent by weight kaolin;
   and as a remainder, silver salts and production mandated other components, wherein the percent by weight indications are relative to the disc when dried.

11. A method for the production of a micro-filter disc having pore sizes of 0.05 to 0.5µ and a diameter greater than 25 cm, said method comprising:
   (a) mixing at least 6 to 12 parts by weight of an already calcined kind of kieselguhr, with 25 to 35 parts by weight kaolin, and 53 to 69 parts by weight a minimally calcined kind of kieselguhr;
   (b) stirring the mixture into about 200 to 250 parts by weight of water while adding about 0.2 to 0.35 parts by weight an organic binding agent;
   (c) stirring the mixture for a period of time until a definite change in viscosity occurs;
   (d) pouring the ready-stirred mixture into a mold made of moisture absorbing material;
   (e) slowly drying the mixture over a period of time of 8 to 25 days; and
   (f) removing the dried mixture from the mold and thereafter burning the mixture under a temperature of 1000° to 1050° C.

12. A method according to claim 11, further comprising the following percentages by weight being used:
   about 40.72 of a first non-calcined or little calcined kieselguhr;
   about 9.05 of a second calcined kieselguhr;
   about 20.82 of a third non-calcined or little calcined kieselguhr; and
   about 29.41 kaolin.

13. A method according to claim 11 further comprising a mixture added of 0.2 to 0.5 parts by weight of silver oxide.

14. A method according to claim 11, wherein said mold comprises a plaster of paris.

15. A method according to claim 11 wherein said mold further comprises a center including an elastic and absorbent hollow cylinder of paper or card board.

16. A method according to claim 11 wherein, after burning, an upper surface of the disc is liberated from a denser cover layer having a thickness of about 5µ by a scraping tool.

17. A method according to claim 11 wherein the burnt micro-filter disc is cut to precise measurements by a high pressure waterjet.

18. A method according to claim 11 wherein at least one outer and at least one inner margins of the disc are provided with seals overlapping to one side of the disc.

19. A micro-filter disc according to claim 1, wherein said micro-filter disc further comprises pore sizes of a magnitude of 0.1 to 0.3μ.

20. A micro-filter disc according to claim 1, wherein said micro-filter disc is monolithical, round, and has a diameter of at least 35 cm.

21. A micro-filter disc according to claim 1, wherein said micro-filter disc further comprises a thickness of 1 to 1.5 cm.

22. A micro-filter disc according to claim 1, wherein said micro-filter disc has a central opening which is round.

23. A micro-filter disc according to claim 1, wherein said micro-filter disc further comprises a central opening having a diameter of 6 to 8 cm.

24. A micro-filter disc according to claim 1, wherein said micro-filter disc further comprises a round central opening having a diameter of 6 to 8 cm.

25. A micro-filter disc according to claim 1, wherein an outer and an inner margin of said micro-filter disc have been cut to measure by a high pressure waterjet cutter.

26. A method for the production of a micro-filter disc according to claim 11, further comprising a micro-filter disc having pore sizes of 0.1 to 0.3μ.

27. A method for the production of a micro-filter disc according to claim 11, further comprising a micro-filter disc having a diameter greater than 35 cm.

28. A method for the production of a micro-filter disc according to claim 11, further comprising mixing about 9 parts by weight an already calcined kind of kieselguhr.

29. A method for the production of a micro-filter disc according to claim 11, further comprising mixing about 30 parts by weight kaolin.

30. A method for the production of a micro-filter disc according to claim 11, further comprising mixing about 61 parts by weight a minimally calcined kind of kieselguhr.

31. A method for the production of a micro-filter disc according to claim 11, further comprising stirring the mixture into about 225 parts by weight of water.

32. A method for the production of a micro-filter disc according to claim 11, further comprising stirring the mixture into about 200 to 250 parts by weight of water while adding about 0.5 to 0.7 parts by weight an organic binding agent.

33. A method for the production of a micro-filter disc according to claim 11, further comprising stirring the mixture for 12 to 15 hours until a definite change in viscosity occurs.

34. A method for the production of a micro-filter disc according to claim 11, further comprising pouring the ready-stirred mixture into a mold made of plaster of paris.

35. A method for the production of a micro-filter disc according to claim 11, further comprising slowly drying the mixture over a period of time of 10 to 20 days.

36. A method for the production of a micro-filter disc according to claim 11, further comprising removing the dried mixture from the mold and thereafter burning the mixture under a temperature of about 1035° C.

37. A method for the production of a micro-filter disc according to claim 11, further comprising a mixture added of about 0.36 parts by weight of silver oxide.

38. A method for the production of a micro-filter disc according to claim 11, wherein at least one outer and at least one inner margins of the disc are provided with seals comprising silicon overlapping to one side of the disc.

* * * * *